(12) United States Patent
Hunziker et al.

(10) Patent No.: US 9,952,171 B2
(45) Date of Patent: Apr. 24, 2018

(54) GAS SENSOR PACKAGE

(71) Applicant: Sensirion AG, Stafa (CH)

(72) Inventors: Werner Hunziker, Stafa (CH); David Pustan, Zurich (CH); Stephen Braun, Stafa (CH)

(73) Assignee: Sensirion AG, Stafa (CH)

( * ) Notice: Subject to any disclaimer, the term of this patent is extended or adjusted under 35 U.S.C. 154(b) by 159 days.

(21) Appl. No.: 14/728,218

(22) Filed: Jun. 2, 2015

(65) Prior Publication Data

US 2015/0362451 A1   Dec. 17, 2015

(30) Foreign Application Priority Data

Jun. 6, 2014   (EP) .................................. 14001973.8

(51) Int. Cl.
| | |
|---|---|
| *G01N 27/26* | (2006.01) |
| *G01N 33/00* | (2006.01) |
| *H01L 23/31* | (2006.01) |
| *G01N 27/12* | (2006.01) |

(52) U.S. Cl.
CPC ......... *G01N 27/26* (2013.01); *G01N 33/0009* (2013.01); *H01L 23/3107* (2013.01); *G01N 27/123* (2013.01); *G01N 27/128* (2013.01); *H01L 2924/0002* (2013.01)

(58) Field of Classification Search
CPC .... G01N 27/26; G01N 27/123; G01N 27/128; G01N 33/0009; H01L 23/3107; H01L 2924/0002
See application file for complete search history.

(56) References Cited

U.S. PATENT DOCUMENTS

| | | | | | |
|---|---|---|---|---|---|
| 4,894,707 A | * | 1/1990 | Yamawaki | .......... | H01L 31/0203 257/667 |
| 4,967,589 A | * | 11/1990 | Yagawara | .............. | G01N 27/12 29/592.1 |
| 4,984,446 A | * | 1/1991 | Yagawara | .............. | G01N 27/12 338/34 |
| 5,218,347 A | * | 6/1993 | Deppe | .................. | G08B 17/117 340/634 |
| 5,388,443 A | * | 2/1995 | Manaka | ............. | G01N 33/0009 73/29.05 |

(Continued)

FOREIGN PATENT DOCUMENTS

| | | |
|---|---|---|
| DE | 102008039068 | 2/2009 |
| DE | 202011051190 | 1/2012 |

(Continued)

OTHER PUBLICATIONS

Machine translation of DE 202011051190.*

*Primary Examiner* — David Bolduc
(74) *Attorney, Agent, or Firm* — Cooper & Dunham LLP (57) ABSTRACT

A gas sensor package comprises a gas sensor chip with a layer sensitive to a gas, and with a heater for heating the sensitive layer. Contact pads are provided for electrically contacting the gas sensor package and a die pad is provided for mounting the gas sensor chip to. Electrical connections connect the gas sensor chip and the contact pads. A molding compound at least partially encloses the gas sensor chip. An opening in the molding compound provides access to the sensitive layer of the gas sensor chip. One of the contact pads serves as a pin for supplying electrical current to the heater of the gas sensor chip.

18 Claims, 3 Drawing Sheets

(56) References Cited

U.S. PATENT DOCUMENTS

| | | | |
|---|---|---|---|
| 5,811,662 A * | 9/1998 | Williams | G01N 27/12 422/90 |
| 5,821,402 A * | 10/1998 | Okajima | C23C 16/04 422/90 |
| 6,111,280 A * | 8/2000 | Gardner | G01N 27/128 257/253 |
| 6,690,569 B1 | 2/2004 | Mayer et al. | |
| 7,096,859 B2 | 8/2006 | Hamisch et al. | |
| 7,434,450 B2 * | 10/2008 | Tashiro | G01N 27/4065 702/116 |
| 7,495,300 B2 * | 2/2009 | Gardner | G01N 27/128 257/252 |
| 8,530,981 B2 | 9/2013 | Huckabee et al. | |
| 2001/0023087 A1 * | 9/2001 | Brandl | G01F 1/6845 438/106 |
| 2005/0285039 A1 | 12/2005 | Ludwig | |
| 2006/0185980 A1 * | 8/2006 | Fukuda | G01N 27/128 204/431 |
| 2008/0128285 A1 | 6/2008 | Moon et al. | |
| 2009/0051052 A1 * | 2/2009 | Yoshioka | H01L 23/3107 257/788 |
| 2009/0243003 A1 * | 10/2009 | Renna | B81C 1/00158 257/414 |
| 2010/0043530 A1 * | 2/2010 | Elian | B81B 7/0048 73/31.06 |
| 2010/0192687 A1 * | 8/2010 | Trakhtenberg | G01N 27/127 73/335.02 |
| 2010/0272611 A1 * | 10/2010 | Helwig | B82Y 15/00 422/98 |
| 2012/0000284 A1 | 1/2012 | Yokoyama et al. | |
| 2012/0217550 A1 * | 8/2012 | Usagawa | G01N 27/4141 257/253 |
| 2013/0056703 A1 | 3/2013 | Elian et al. | |
| 2013/0333446 A1 * | 12/2013 | Trakhtenberg | G01N 27/127 73/31.06 |
| 2014/0208828 A1 | 7/2014 | Von Waldenkirch | |
| 2015/0129770 A1 * | 5/2015 | Henderson | G01N 21/3504 250/343 |

FOREIGN PATENT DOCUMENTS

| | | |
|---|---|---|
| WO | 0142776 | 6/2001 |
| WO | 0250528 | 6/2002 |
| WO | 2006114005 | 11/2006 |
| WO | 2010140545 | 12/2010 |

* cited by examiner

GAS SENSOR PACKAGE

CROSS REFERENCE TO RELATED APPLICATIONS

This application claims the priority of European Patent Application No. 14001973.8, filed Jun. 6, 2014, the disclosure of which is incorporated herein by reference in its entirety.

FIELD OF THE INVENTION

The present invention relates to a gas sensor package.

TECHNICAL BACKGROUND

An increasing number of gas sensors tend to be integrated into semiconductor chips. In view of specifics of the gas sensors as such and their operation, a package is required for a gas sensor chip that addresses these specifics.

DISCLOSURE OF THE INVENTION

Hence, according to a first aspect of the invention, a gas sensor package is provided comprising a gas sensor chip with a layer sensitive to a gas or composites therein, and with a heater.

The gas sensor chip, also referred to as die, may contain a semiconductor substrate, such as a silicon substrate, into which semiconductor substrate a processing circuit may be integrated. Layers, such as CMOS layers may be provided for building the integrated processing circuit.

The gas sensor chip preferably has a front side and a back side, wherein the sensitive layer preferably is arranged at the front side. The sensitive layer may be arranged on top of the semiconductor substrate or on top of a layer, such as one of the CMOS layers, assigned to the semiconductor substrate. In case an integrated processing circuit is provided in the same gas sensor chip, the sensitive layer may be connected thereto for pre-processing signals from the sensitive layer in the integrated processing circuit. The integrated processing circuit may, e.g. also control a heater to be introduced later on.

The sensitive layer may be made from material being sensitive to one or more analytes. The sensitive layer may comprise multiple individual layer sections arranged next to each other and being separated from each for building a sensor array comprising a set of sensor cells, wherein a sensor cell may be understood as an entity of the gas sensor which may be read individually. Preferably, in the embodiment of the sensor array, each or at least some of the layer sections are suitable for sensing to analytes, and in particular different analytes. Analytes may include one or more of, for example, CO2, NOX, ethanol, CO, ozone, ammonia, formaldehyde, $H_2O$, or xylene without limitation.

Specifically, the sensitive layer may contain a metal oxide material, and in particular a semiconducting metal oxide material, and specifically may contain metal oxide materials of different composition per layer section. A metal oxide material generally may include one or more of tin oxide, zinc oxide, titanium oxide, tungsten oxide, indium oxide and gallium oxide. Such metal oxides may be used for the detection of analytes such as VOCs, carbon monoxide, nitrogen dioxide, methane, ammonia or hydrogen sulphide. Metal oxide sensors are based on the concept that gaseous analytes interact with the metal oxide layer at elevated temperatures of the sensitive layer in the range of more than 100° Celsius, and specifically between 250° C. and 350° Celsius. As a result of the catalytic reaction, the conductivity of the sensitive layer may change which change can be measured. Hence, such chemical sensors are also denoted as high temperature chemoresistors for the reason that a chemical property of the analyte is converted into an electrical resistance at high temperatures of the sensitive layer. Preferably, by means of such a gas sensor a gas may be investigated at least as to the absence or presence of the subject analyte/s the gas sensor is sensitive to.

In another embodiment, the sensitive layer may comprise a polymer that in one embodiment may be sensitive to $H_2O$ such that the sensor may be a humidity sensor. A capacity or a resistance of such polymer layer may be measured for deriving information as to the gas that may interact with the sensitive layer.

Hence, the gas supplied to the gas sensor may be analyzed by means of the sensitive layer as to if and which of the chemical substances or compounds the layer is sensitive to are present in the gas supplied. A combination of analytes detected in the gas supplied may suggest for a certain odour or for a certain gas. It is always subject to a design of the gas sensor as to how many different analytes and/or how many different properties of an analyte the gas sensor is sensitive to.

For supporting a measurement by the sensitive layer and/or supporting a manufacturing of the gas sensor package, a heater is provided, such as a resistive heater. In one embodiment, the heater is required for heating the sensitive layer prior to and/or during a gas measurement. This may be the case, for example, when the sensitive layer contains metal oxide material. In another embodiment, the heater may alternatively or additionally be used for annealing the sensitive layer after having applied a sensitive material to the gas sensor chip for building the sensitive layer from. This may be the case when the sensitive layer is comprises a polymer, and/or when the sensitive layer is made from a material comprising metal oxide.

In a preferred embodiment, the gas sensor chip may contain additional features to support the operation of the sensitive layer, e.g. a suspended membrane to achieve thermal insulation. In such embodiment, the sensitive layer and the heater may be arranged on or in such membrane. In a preferred embodiment, the membrane is manufactured by etching, such as dry-etching or wet-etching, or otherwise removing material from the backside of the gas sensor chip, such as bulk substrate material, thereby generating a recess into the gas sensor chip. The remaining material of the gas sensor chip above the recess forms a membrane which may be formed by CMOS layers and/or parts of the bulk substrate material.

The gas sensor chip is mounted to a die pad. The die pad may be made from an electrically and thermally conducting material, such as metal. The gas sensor chip may be attached to the die pad in one example such that a substrate of the gas sensor chip may be grounded via the die pad. The die pad may have a footprint approximately equal to a footprint of the gas sensor chip. After having mounted the gas sensor chip to the die pad, the recessed portion of the gas sensor chip and the die pad form a cavity underneath the membrane. Heat generated by the heater in the membrane during operation may be transferred via gas in the cavity to the die pad acting as a heat sink. In one embodiment, a hole or another sort of channel is provided in the die pad for venting the cavity there through in the context of pressure balancing, and for removing moisture from the cavity. The hole may be fabricated subject to the material of the die pad and/or the carrier in general, e.g. by etching, piercing, laser drilling, mechanical drilling, etc.

In another embodiment, an additional chip comprising an integrated processing circuit, e.g. an ASIC may additionally be mounted to the same or a different die pad of the same carrier. An electrical connection in the form of e.g. bond wires may electrically connect the gas sensor chip and the additional chip.

Contact pads are provided in addition to the die pad for electrically contacting the gas sensor package, and specifically the gas sensor chip, either directly or via an additional chip as indicated above, preferably via electrical connections between the gas sensor chip and the contact pads. The contact pads are preferably made from the same material as the die pad, and are preferably arranged in the same plane as the die pad. The contact pads are made from electrically conducting material and are exposed to the environment as pins for electrical contact.

In one embodiment, the contact pads and the die pad are manufactured from a leadframe. The contact pads may be represented by electrically conducting platforms or leads electrically isolated from each other. Such leadframe may act as a carrier for the gas sensor chip.

A molding compound may be applied to such carrier with the gas sensor chip being mounted thereto. The molding compound preferably is an epoxy with filler particles which filler particles e.g. may be glass. The molding compound at least partially encloses and/or encapsulates the gas sensor chip. An opening is provided in the molding compound for allowing a gas to be measured to access the sensitive layer of the gas sensor chip. The molding compound encapsulates and as such covers the gas sensor chip essentially except for the sensitive layer such that any outgassing from the gas sensor chip itself, from adhesives between the gas sensor chip and the carrier, or from the carrier itself etc. does not have any impact on the measurement because these elements do not share a common volume with the sensitive layer as opposed to a cap package housing, for example, in which the gas sensor chip, the cap, the carrier and any adhesives between these elements share a common volume. Such common volume is also referred to as dead volume within such package, and an outgassing from any of these elements, in particular in view of the heating required for operating the sensitive layer, may affect the measurement temporarily, or even permanent. However, in the present embodiment, the dead volume is reduced and limits any outgassing effect on the sensitive layer. Hence, it is preferred, that the sensitive layer on the one hand and on the other hand the carrier, the gas sensor chip and any adhesive in between do not share a common volume.

For manufacturing the opening, a mold used in the molding process may have a protrusion. In this case, the gas sensor chip may be protected from mechanical impact during molding and the area for the designated sensitive layer may be sealed by a preferably elastic layer arranged on top of the gas sensor chip in the area, and/or arranged at the mold at the protrusion or at least parts thereof. After the molding, the layer may be removed again. In a different embodiment, a sealing frame may be deposited around an area the sensitive layer is expected to be arranged at. The protrusion of the mold for manufacturing the opening may then sit on the sealing frame during molding. The sealing frame may be made from elastic material. The sealing frame may not necessarily be removed after molding. In another embodiment, a wall element is arranged on top of the gas sensor chip encircling the area the sensitive layer is expected to be arranged at. Such wall element may, for example, either be bonded to the gas sensor chip or be manufactured by photolithographic steps, may be of a material different to the molding compound, and may act as a barrier preventing the molding compound from entering the area designated for the sensitive layer. In this embodiment, the mold may not necessarily need a protrusion but even can be flat and directly sit on the wall element during molding. The wall element may not be removed after molding but continues to define the opening in the molding compound given that the molding compound stops at the wall. The wall preferably is of a material different than the molding compound.

Hence, in this embodiment the gas sensor chip is bonded to the die pad, and such device may be molded with the molding compound not only serving as partial encapsulation of the gas sensor chip but also serving as mechanical fixture for the contact pads and the die pad.

It is preferred, that at least portions of the contact pads are accessible from the outside, and especially from below, i.e. a back side of the gas sensor package. Other or the same portions of the contact pads may act on their top e.g. as bond pads in case the electrical connections between the gas sensor chip and the contact pads are wire bonds. It may be preferred to bond from bond pads on the front side of the gas sensor chip down to these portions of the contact pads. In case the locations of the bond pads on the leadframe and the portions exposed to the outside differ, the contact pads manufactured from the leadframe also act as redistribution layer.

In another embodiment comprising the leadframe, prior to molding the molding compound a pre-molding compound may be applied to the leadframe for building a flat carrier. Such carrier preferably is prefabricated by providing a leadframe, placing the leadframe into a mold, and filling the mold with a pre-mold compound. After having mounted to gas sensor chip to such carrier, the molding compound may be applied, thereby at least partially covering the pre-molding compound.

In an alternate embodiment, the contact pads and the die pad may be part of a printed circuit board. Here, the die pad may be formed by a metallization of a front side of the printed circuit board, while the contact pads are formed by metallizations on a backside of the printed circuit board which additionally requires vias through the printed circuit board for connecting the contact pads. Instead of a printed circuit board, another carrier such as a ceramic substrate or a glass substrate may be used.

It is envisaged that the heater is not supplied with power via the contact pad serving as power supply for the sensor chip. Instead, the heater is supplied with power via a dedicated contact pad serving as heater pin. This contact pad may, via the electrical connection and metallizations in the gas sensor chip directly be connected to the heater. Given that the heater may demand currents of e.g. more than 10 mA and possible up to 100 mA, it was found beneficial that the power supply for the regular operation of the gas sensor chip, which may be supplied by a current in the order of few mA, such as 1.8 mA, may be separated from the power supply for the heater. In this way, overall reliability of the operation of the gas sensor package is enhanced. For reliably measuring gas, a stable and precise power supply is required for the gas sensor chip and preferably for its processing circuit. If the current for the heater were to be derived in the gas sensor chip from the normal power supply, the normal power supply may show fluctuations which are not desired. In a preferred embodiment, the contact pad serving as pin for operating the heater and the other contact pad serving as supply pin for supplying power for operating the gas sensor chip except for the heater are spaced apart from each other, and e.g. are arranged at different edges of the back side of the gas sensor package. In this way, any heating of the gas sensor chip and its environment is introduced from different ends and does not accumulate in a hot spot if the contact pads were neighbors. In an embodiment, a processing circuit integrated in the gas sensor chip or a separate ASIC may control the heating of the heater.

It is preferred that the opening in the molding compound is arranged in a front side of the gas sensor package while the contact pads and the die pad are arranged at a back side thereof. This provides a compact small size package suited for being arranged into portable electronic devices such as mobile phones, tablet computers, etc. In this context, the gas sensor package may in a preferred embodiment have the shape of a cuboid. The opening in the molding compound preferably has a circular footprint and may in one embodiment be centered in the front side of the gas sensor package, and in another embodiment be arranged off-centered in the front side. The geometry of the access opening mainly is dependent on the size of the dimensions of the membrane the sensitive layer is to be deposited to in one embodiment, such that in an effort to minimize the overall size of the gas sensor package, it is desired to reduce the footprint of the molding compound outside the opening if possible. However, it is also desired to keep the footprint of the access opening as small as possible since the volume defined by the opening may be considered as dead volume for the sensitive layer and any outgassing of the molding compound affecting the sensitive layer may be reduced the smaller the molding compound surface defining the dead volume is. Generally, such small package size is not only desired in view of the application of such gas sensor package in portable electronic devices, but also in view of a possible manufacturing in which the sensitive layer may be applied to the gas sensor chip through the opening of the already manufactured molding compound. In case the gas sensor packages are still residing on a common carrier during this manufacturing step, any working tool applying the sensitive layers to the gas sensor packages operates quicker the smaller a travel distance is between the openings of adjacent gas sensor packages. The molding compound in turn provides a mechanical stability for the gas sensor packages when applying the sensitive layers, e.g. by ink jet printing since the gas sensor chip including the membrane are already fixed within the molding compound. In addition, a small package size is beneficial in that the dead volume is reduced and limits any outgassing effect on the sensitive layer.

Hence, in a preferred embodiment, the cuboid gas sensor package has a footprint with a length l times a width w in $mm^2$. In particular, the cuboid gas sensor package has a footprint l×w $mm^2$ with l∈[2.3, 2.6] mm, w∈[2.3, 2.6] mm. It is preferred that the diameter d of the opening is less than 2 mm, and in particular is d∈[1.4, 1.6] mm. In case the opening varies in diameter down to the gas sensor chip, and e.g. narrows, it is assumed that the diameter d is the maximum diameter of such opening, which in the latter case would be the diameter in the top surface of the molding compound. All these embodiments aim at a small size gas sensor package while at the same time limiting the dead volume relevant for the impact of outgassing and allowing a sufficient thermal insulation of the sensitive layer.

In one embodiment, the gas sensor package has six contact pads. As indicated above, a first one of the contact pads serves as pin for supplying a current to the heater. Another one of the contact pads may serve as a supply pin for supplying power for operating the gas sensor chip except for the heater. A third one of the contact pads serves as a ground pin. A fourth one of the contact pads serves as a data pin for at least receiving measurement data from the gas sensor chip communicated according to a communication protocol. A fifth one of the contact pads serves as pin for a clock for operating the communication protocol, such as the I2C protocol. A sixth one of the contact pads serves as a programmable pin for programming the gas sensor chip.

Preferably, the six contact pads are arranged in two rows by three at the backside of the gas sensor package and the die pad is arranged between the two rows of three contact pads each. This allows for a dense arrangement, in particular if the die pad is of rectangular shape.

In a preferred embodiment, the front side of the gas sensor package comprises at least one marking. In case the footprint of the gas sensor package is of rectangular shape each marking is arranged in a corner of the front side. Preferably, a single marking is applied to one of the corners for defining an orientation of the gas sensor package.

In the present application, molding compound or premolding compound shall at least include any plastic material or dry resist that may in any form be molded, such as injection-molded, transfer-molded, or otherwise molded.

The present gas sensor package in its various embodiments not only is small in its dimensions but at the same time reduces outgassing possibly impacting measurements, ensures a stable/"clean" power supply $V_{DD}$ while at the same time supplying a high current to the heater not interfering with the power supply for the gas sensor chip. The heating of the sensitive layer is only locally applied, where temperatures of more than 200° degrees Celsius and sometimes even far more may be achieved. In contrast, outside the membrane with the heater and the sensitive layer the temperature may not exceed e.g. 85° degrees Celsius for avoiding an impact on processing sensor signals. A corresponding processing circuit preferably is arranged outside the membrane and preferably supplies digital signals to one of the contact pads. The present gas sensor package preferably is SMD mountable to external support.

Other advantageous embodiments of the gas sensor package are listed in the dependent claims as well as in the description below.

BRIEF DESCRIPTION OF THE DRAWINGS

Embodiments of the present invention, aspects and advantages will become apparent from the following detailed description thereof. Such description makes reference to the annexed drawings, wherein the figures show.

DETAILED DESCRIPTION OF THE DRAWINGS

Figure 1:
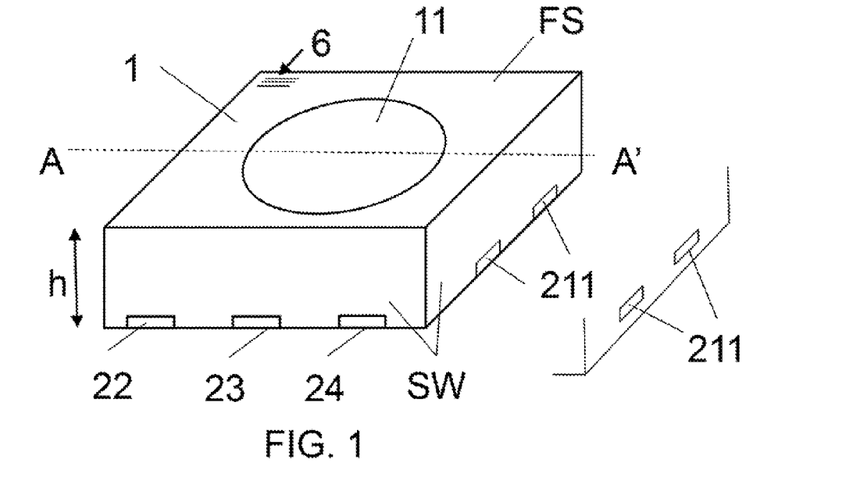
FIG. 1 a perspective view of a gas sensor package according to an embodiment of the present invention.

FIG. 1 illustrates a perspective view of a gas sensor package according to an embodiment of the present invention. The gas sensor package has the shape of a cube with a front side FS and a back side opposite to the front side FS, which is not visible in this perspective view. A molding compound 1 defines the shape of the gas sensor package. The molding compound 1 has a central opening 11 for providing access to a sensitive layer of a gas sensor chip.

In one of the corners of the molding compound on the front side FS, a marking 6 is provided, e.g. by laser processing, ink jet printing, etc. The marking may indicate one or more of orientation of the gas sensor package, a device number, a serial number, the manufacturer, etc.

In side walls SW of the gas sensor package are also built by the molding front ends of contact pads 22, 23, 24 are exposed from the molding compound 1 as well as die pad supports 211 the function of which will be explained later on.

However, in a different embodiment, one or more of the contact pads and/or the die pad supports 211 may not finalize with the bottom edge of the gas sensor package as shown in FIG. 1, but may be elevated from such edge such as shown in the cutout to the right of FIG. 1, where the die pad supports 211 are arranged at a distance of e.g. between 100 µm and 200 µm from the bottom edge.

The gas sensor package of the present example has a height of preferably between 0.7 and 0.8 mm.

Figure 2:
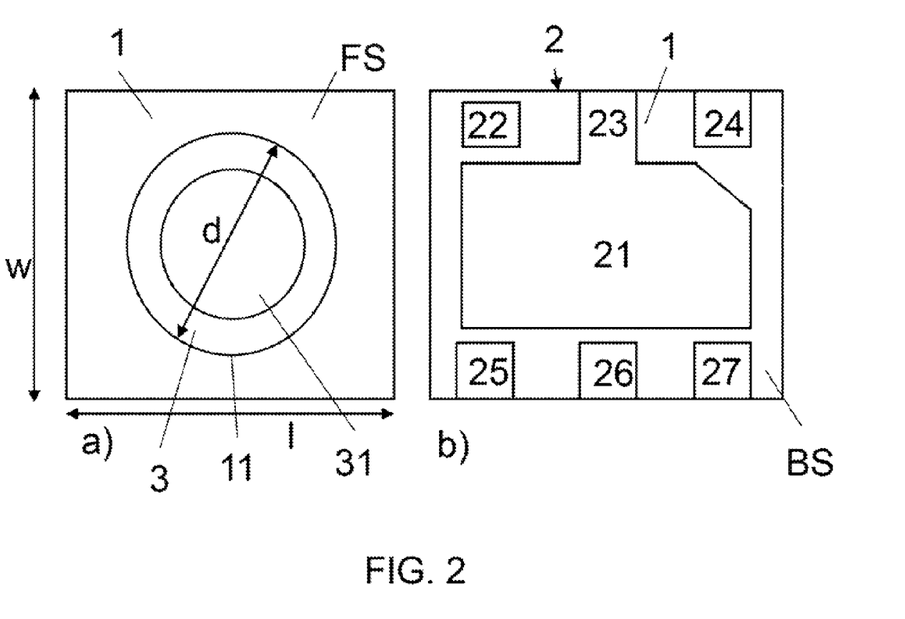
FIG. 2 a top view a) and a bottom view b) on the gas sensor package of FIG. 1.

FIG. 2 illustrates a top view a) and a bottom view b) on the gas sensor package of FIG. 1. According to the top view on the front side FS according to diagram 2a), the opening 11 is defined by the molding compound 1. The opening 11 is of circular shape and has a diameter d, preferably between 1.4 and 1.6 mm. The cubic gas sensor package has a footprint l×w with each of the length l and the width preferably being in the range between 2.3 and 2.7 mm. When looking into the opening 11, the sensitive layer 31 is visible. The sensitive layer 31 preferably has a diameter little smaller than the diameter d of the opening such that a small portion of the gas sensor chip 3 outside the sensitive layer 31 is visible.

The back side BS of the gas sensor chip shows six contact pads 22-27 according to diagram 2b). The contact pads 22-27 are arranged in two rows of three contact pads each at two opposite edges of the gas sensor package. Preferably, each contact pad is dimensioned by less than 0.5 mm by 0.5 mm, and a pitch between each two contact pins of a row is in the range of 0.8 mm.

Preferably, the contact pad 26 serves as heater pin for operating the heater. Contact pad 24 serves as a supply pin for supplying power for operating the gas sensor chip 3 except for the heater. Contact pad 23 serves as a ground pin and is connected to a die pad 21 for grounding a substrate of the gas sensor chip. Contact pad 22 serves as a data pin for at least receiving measurement data from the gas sensor chip communicated according to a communication protocol, such as the I2C protocol. Contact pad 27 serves as pin for a clock for operating the communication protocol, such as the I2C protocol. Contact pad 25 serves as a programmable pin for programming the gas sensor chip 3, e.g. with calibration data. The contact pads 22 to 27 may in another embodiment be arranged in the same sequence but rotated around the die pad 21.

Figure 3:
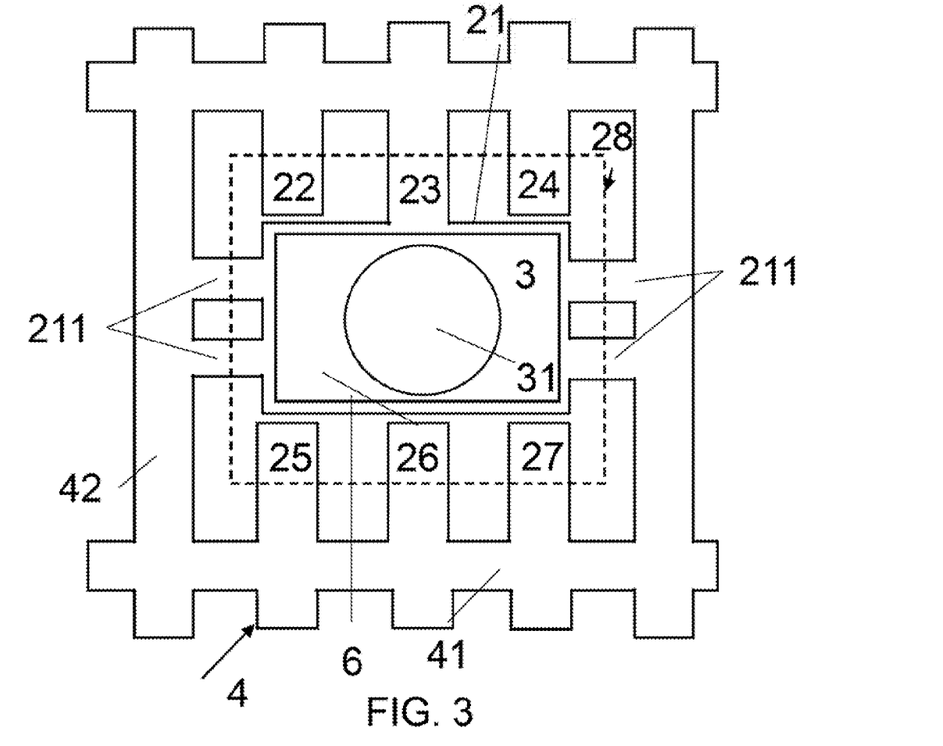
FIG. 3 a top view on gas sensor package in an intermediary manufacturing step according to an embodiment of the present invention.

In between the two rows, the die pad 21 is provided which serves as support for the gas sensor chip 3 which will be explained in more detail later on. The die pad 21 is of rectangular shape and has one flattened corner which may serve as an optical and/or mechanical encoding for an orientation of the gas sensor package. The contact pads 22-27 and the die pad 21 are mechanically linked by the molding compound 1. FIG. 3 illustrates a top view on gas sensor package, e.g. the gas sensor package of FIGS. 1 and 2, in an intermediary manufacturing step according to an embodiment of the present invention. Here, it becomes apparent that the contact pads 22-27 and the die pad 21 belong to a common leadframe 4 which, for example, comprises horizontal leads 41 from which the contact pads 22-27 depart. The die pad 21, instead, is connected by means of die pad supports 211 to the vertical leads 42 of the lead frame 4. A gas sensor chip 3 containing the sensitive layer 31 is arranged on the die pad 21. The final mold 1 is not yet applied to the present device. However, it is assumed that prior to mounting the gas sensor chip 3 to the die pad 21 the pre-molding compound 28 is applied to the leadframe. The pre-molding compound 28 is indicated by a dashed rectangle. For doing so, a mold may be applied to the leadframe 4, and preferably to a major leadframe 4 comprising multiple of leadframe structures as shown in FIG. 3 for finally manufacturing multiple gas sensor packages. After having placed the gas sensor package 3 to the pre-molded leadframe 4, the final mold may be applied on top of the pre-molded leadframe 4, and the resulting gas sensor package may be diced along the dashed lines, thereby separating the gas sensor package from the leads 41 and 42. In view of the pre-molding compound 28 and the molding compound 1 preferably being of the same material, it is legitimate not to distinguish there between in FIG. 1.

In FIG. 3, a single bond wire 6 is schematically shown between the heater contact pad 26 and the gas sensor chip 3. Although it is understood, that the other contact pins 22 to 25 and 27 are also electrically connected to the gas sensor chip 3 by means of bond wires not shown for a better illustration.

Figure 4:
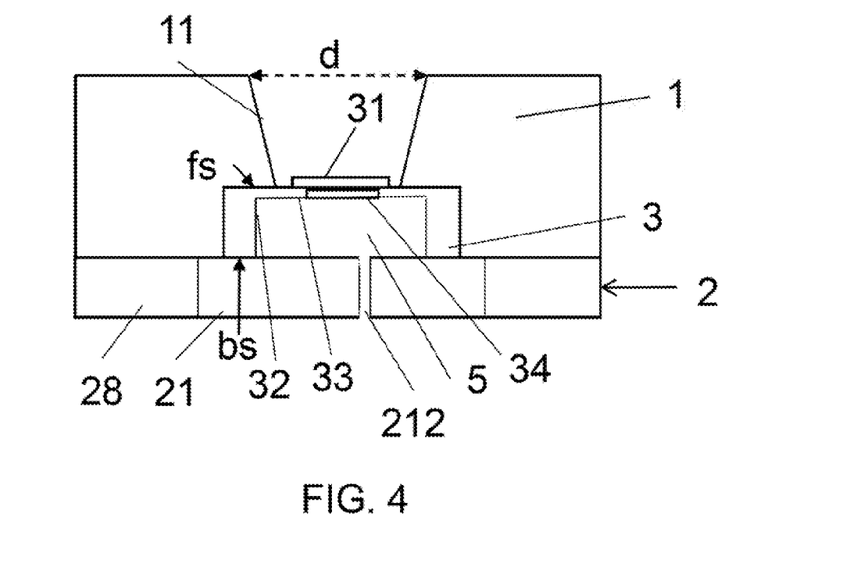
FIG. 4 a cut through a gas sensor package according to an embodiment of the present invention.

FIG. 4 illustrates a cut through a gas sensor package according to an embodiment of the present invention. Except of the shape of the opening 11 and a venting hole 212 provided in the die pad 21, the gas sensor package shown in FIG. 4 may be the gas sensor package shown in any of the preceding FIGS. 1 to 3. Specifically, the gas sensor package in FIG. 4 may be a cut through the gas sensor package of FIG. 1 along the lines A-A'.

In this cut, only the die pad 21 and portions of the pre-mold compound 28 are visible of the carrier 2 for the gas sensor chip 3. The gas sensor chip 3 is arranged on top of the die pad 21, and e.g. is bonded thereto. The gas sensor chip 3 has a front side fs and a back side bs. In one embodiment, the gas sensor chip 3 may comprise a semiconductor substrate and CMOS layer arranged on top of the substrate. The substrate may be etched or otherwise partially removed from the backside bs such that the gas sensor chip 3 has a recess 32 on its backside bs. This process step may be implemented prior to bonding the gas sensor chip 3 to the die pad 21. As a result of building the recess 32 in the gas sensor chip 3, a thinned structure is generated in the gas sensor chip 3, also referred to as membrane 33. The sensitive structure 31 is arranged on or in the membrane.

In a specific embodiment, the sensitive layer 31 comprises a metal oxide layer which is to be heated for enabling the sensing of chemical analytes. For this purpose, a heater 34 such as a resistive heater is arranged in or under the membrane 33 for heating the sensitive layer 31. Hence, both the gas sensitive layer 31 and the heater 34 may be arranged on or in the membrane above the recess. This arrangement is owed to a thermal insulation the membrane 33 provides which improves the accuracy of the measurement.

In a preferred embodiment, the die pad 21 has a hole 212 for connecting the cavity 5 to the outside world. Heat may be transferred via gas in the cavity 5 to the die pad 21 which acts as a heat sink, or heat accepted by the gas in the cavity 5 may escape from the cavity 5 through the venting hole 212.

The mold 1 partially encapsulates the gas sensor chip 3 providing an opening 11 towards the gas sensitive layer 31 of the gas sensor chip 3. In this embodiment, the opening 11 has a circular footprint which narrows towards the gas sensitive layer 31.

Figure 5:
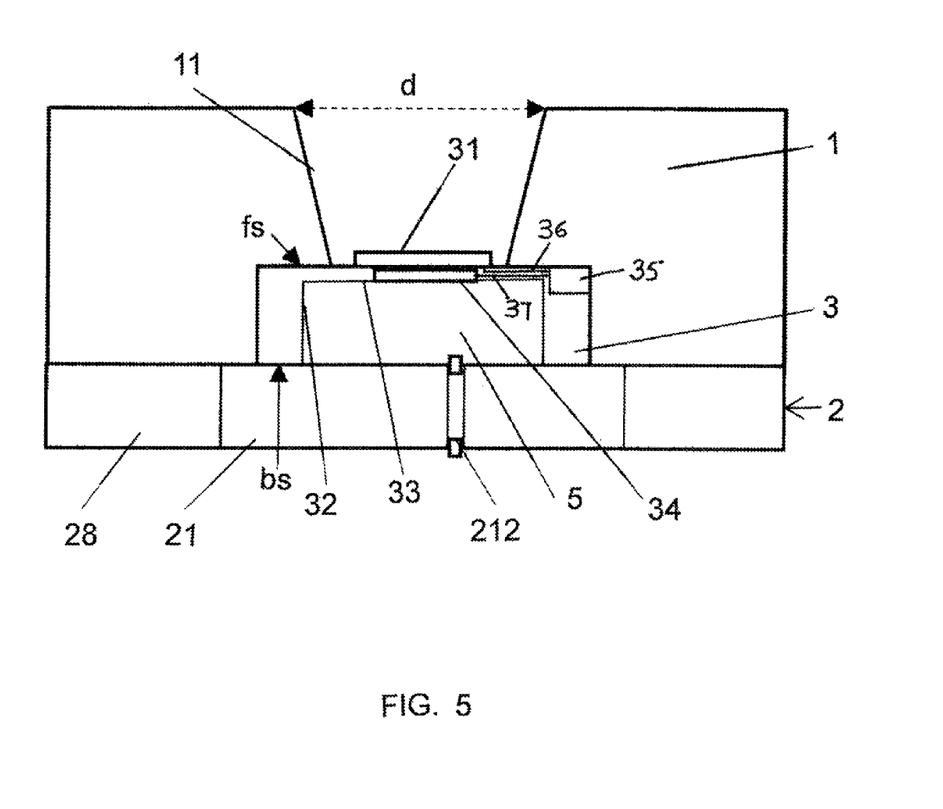
FIG. 5 an enlarged view similar to FIG. 4 including a highly simplified and schematic showing of an integrated processing circuit and its connections to the sensitive layer and heater, in the illustrated embodiment of the invention.

FIG. 5, which is a view similar to FIG. 4 but enlarged, shows a processing circuit 35 integrated into the semiconductor substrate of the gas sensor chip 3. The sensitive layer is connected to the integrated processing circuit 35 as indicated at 36 in FIG. 5. The processing circuit 35 also controls the heater 34 as indicated at 37 in FIG. 5.

While above there are shown and described embodiments of the invention, it is to be understood that the invention is not limited thereto but may be otherwise variously embodied and practised within the scope of the following claims.

The invention claimed is:

1. A gas sensor package, comprising
a gas sensor chip comprising a semiconductor substrate, a processing circuit integrated into the semiconductor substrate, a layer sensitive to a gas and connected to the processing circuit, and a heater for heating the sensitive layer,
contact pads for electrically contacting the gas sensor chip,
a die pad for mounting the gas sensor chip to,
electrical connections between the gas sensor chip (3) and the contact pads,
a molding compound at least partially enclosing the gas sensor chip, and
an opening in the molding compound providing access to the sensitive layer of the gas sensor chip,
wherein one of the contact pads serves as a pin for supplying electrical current to the heater of the gas sensor chip,
wherein another one of the contact pads serves as a supply pin for supplying power for operating the gas sensor chip except for the heater, and
wherein the processing circuit is configured to control the heater.

2. The gas sensor package of claim 1,
comprising a front side and a back side, wherein the opening is arranged in the front side, and wherein the contact pads are arranged at the back side.

3. The gas sensor package of claim 2,
wherein the contact pads and the die pad are exposed from the molding compound at the back side of the gas sensor package.

4. The gas sensor package according to claim 1,
wherein the gas sensor package has the shape of a cuboid, and
in particular wherein the opening in the molding compound has a circular footprint.

5. The gas sensor package of claim 4,
wherein the gas sensor package has a footprint of l×w mm², and
wherein the length l of the footprint of the gas sensor package is l∈[2.3, 2.6] mm, and the width w is w∈[2.3, 2.6] mm.

6. The gas sensor package of claim 4,
wherein a diameter d of the opening is less than 2 mm, and in particular wherein the diameter d of the opening is d∈[1.4, 1.6] mm.

7. The gas sensor package according to claim 4,
wherein the opening is arranged centered in the front side of the gas sensor package.

8. The gas sensor package according to claim 1,
wherein the gas sensor chip comprises a front side and a back side,
wherein a recess is provided in the backside of the gas sensor chip,
wherein the sensitive layer is arranged at the front side of the gas sensor chip in a portion above the recess, and
wherein the gas sensor chip is mounted with its backside to the die pad thereby building a cavity defined by the recessed portion of the gas sensor chip and the die pad.

9. The gas sensor package of claim 8,
wherein the die pad comprises a hole for venting the cavity.

10. The gas sensor package according to claim 1,
wherein a third one of the contact pads serves as a ground pin.

11. The gas sensor package according to claim 1,
wherein a fourth one of the contact pads serves as a data pin for at least receiving measurement data from the gas sensor chip communicated according to a communication protocol, and
in particular wherein a fifth one of the contact pads serves as clock pin for a clock for operating the communication protocol.

12. The gas sensor package according to claim 1,
wherein a sixth one of the contact pads serves as a programmable pin for programming the gas sensor chip.

13. The gas sensor package according to claim 2,
wherein a third one of the contact pads serves as a ground pin,
wherein a fourth one of the contact pads serves as a data pin for at least receiving measurement data from the gas sensor chip communicated according to a communication protocol,
wherein a fifth one of the contact pads serves as clock pin for a clock for operating the communication protocol,
wherein a sixth one of the contact pads serves as a programmable pin for programming the gas sensor chip,
wherein the six contact pads are arranged in two rows by three at the backside of the gas sensor package.

14. The gas sensor package according to claim 13,
wherein the die pad is arranged between the two rows of three contact pads each, and
in particular wherein the die pad is of rectangular shape, and
in particular wherein the rectangular shape of the die pad is modified for encoding an orientation of the gas sensor package.

15. The gas sensor package according to claim 1,
wherein the contact pads are represented by individual electrically conducting platforms, and
wherein the electrical connections between the gas sensor chip and the contact pads comprise bond wires.

16. The gas sensor package according to claim 2,
wherein the front side and the back side of the gas sensor package are linked by side walls (SW), and
wherein one front end of each contact pad is exposed from the side walls.

17. The gas sensor package according to claim 2,
wherein the front side of the gas sensor package comprises at least one marking, and in particular wherein the front side is of rectangular shape and wherein each marking is arranged in a corner of the front side.

18. The gas sensor package according to claim 2, wherein the other contact pad serving as supply pin for supplying power for operating the gas sensor chip except for the heater and the contact pads serving as pin for operating the heater are arranged at different edges of the back side of the gas sensor package.

* * * * *

UNITED STATES PATENT AND TRADEMARK OFFICE
CERTIFICATE OF CORRECTION

PATENT NO. : 9,952,171 B2
APPLICATION NO. : 14/728218
DATED : April 24, 2018
INVENTOR(S) : Werner Hunziker, David Pustan and Stephan Braun It is certified that error appears in the above-identified patent and that said Letters Patent is hereby corrected as shown below:

On the Title Page

Column 1, (72), second line, "Stephen" should read --Stephan--.

Signed and Sealed this
Tenth Day of July, 2018

Andrei Iancu
*Director of the United States Patent and Trademark Office*